United States Patent [19]

Ponzi

[11] 4,345,456
[45] Aug. 24, 1982

[54] DENSITOMETER

[75] Inventor: Joseph J. Ponzi, Alhambra, Calif.

[73] Assignee: International Telephone and Telegraph Corporation, New York, N.Y.

[21] Appl. No.: 186,892

[22] Filed: Sep. 15, 1980

[51] Int. Cl.$^3$ ............................................. G01N 9/00
[52] U.S. Cl. ................................................... 73/32 A
[58] Field of Search ....................................... 73/32 A

[56] References Cited

U.S. PATENT DOCUMENTS 4,135,383 1/1979 November ......................... 73/32 A

*Primary Examiner*—James J. Gill
*Attorney, Agent, or Firm*—A. Donald Stolzy

[57] ABSTRACT

A vibration densitometer probe including an internal piezoelectric crystal, a canted vane, and an isotropic ring to support the vane.

8 Claims, 8 Drawing Figures

DENSITOMETER

BACKGROUND OF THE INVENTION

This invention relates to densitometers, and more particularly to a probe for a vibration densitometer.

SUMMARY OF THE INVENTION

In accordance with the present invention, there is provided a densitometer probe having an internal piezoelectric crystal, a canted vane, and/or an isotropic mounting ring for the vane.

BRIEF DESCRIPTION OF THE DRAWINGS

In the accompanying drawings which illustrate exemplary embodiments of the present invention.

DESCRIPTION OF THE PREFERRED EMBODIMENTS

Figure 1:
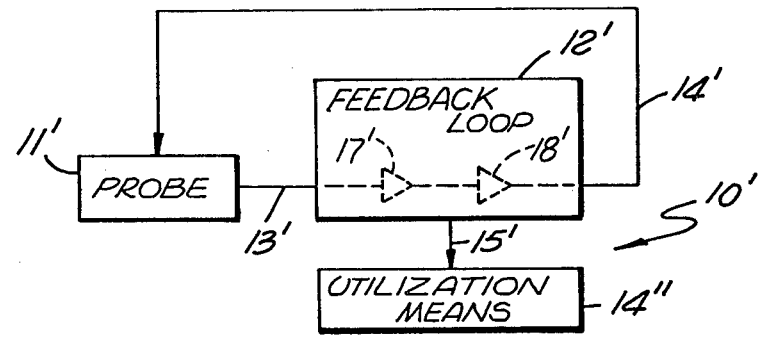
FIG. 1 is a block diagram of a vibration densitometer.

In FIG. 1, a vibration densitometer 10' is shown including a probe 11', a feedback loop 12' connected from and to probe 11' via leads 13' and 14', respectively, and utilization means 14" connected from another output 15' of loop 12'. Densitometer 10' may be similar to or identical to that disclosed in U.S. Pat. No. 3,741,000, issued June 26, 1973, or in C. E. Miller et al, U.S. Pat. No. 3,677,067, issued July 18, 1972. Probe 11' may be, conventional or constructed in accordance with the present invention as described and/or illustrated herein. Attention is also invited to the said U.S. Pat. No. 3,741,000 and to M. H. November U.S. Pat. No. 4,037,460, issued July 26, 1977. By this reference hereto, the entire contents of all of the aforementioned patents are incorporated herein in their entireties. The same is true of copending application Ser. No. 004,179, filed Jan. 17, 1979, by M. H. November for DENSITOMETER CALIBRATION METHOD and assigned to the assignee of this application now U.S. Pat. No. 4,194,385.

Figure 2:
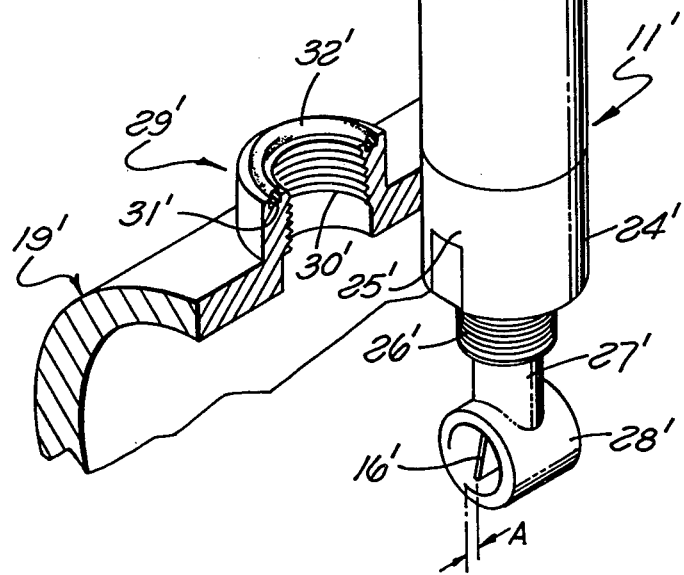
FIG. 2 is a perspective view of a first densitometer probe constructed in accordance with the present invention, the densitometer probe being illustrated adjacent a pipeline.

Probe 11' may, in accordance with the present invention contain a vane 16' as shown in FIG. 2 which is vibrated. Vane 16' is vibrated because the probe has a piezoelectric crystal pickup, not shown, the output of which is amplified and the vane 16' vibrated by a magnetostrictive driver, not shown. The resonant vibrational frequency f of vane 16' is a known function of the density of the gas or liquid or other fluid in which the vane 16' is immersed.

If desired, loop 12' in FIG. 1 may have a linearization circuit so that the output signal on lead 15' may have a magnitude directly proportional to density.

Utilization means 14" may be a voltmeter or ammeter calibrated in density, a process controller, a gas flow computer, a net oil computer, or otherwise.

In accordance with the foregoing, the word "densitometer" is hereby defined to include or not include utilization means 14". Note will be taken that the densitometer in many cases will be manufactured and sold without any utilization means 14". Such utilization means 14" would be supplied by the customer.

The vibration densitometer 10' is essentially an electromechanical oscillator. The oscillator obviously has losses. Loop 12', therefore, includes at least one amplifier. Two amplifiers 17' and 18' are illustrated in loop 12' in FIG. 1.

Probe 11' is shown in FIG. 2 for mounting in a pipeline 19'. The probe 11' may be identical to the probe shown in the said U.S. Pat. No. 3,741,000, or with certain exceptions.

The probe 11' in FIG. 2 has conduits 20' and 21', and a pull box 22'. Conduits 20' and 21' and pull box 22' simply serve as enclosures for the output leads from probe 11' to loop 12' shown in FIG. 1.

Conduit 21' is threaded to pull box 22' in a manner not shown. Conduit 20' is threaded to pull box 22' and to a body 23' of probe 11'. Conduits 20' and 21', pull box 22' and body 23' are, thus, all fixed together. A body 24' is fixed to body 23'. Body 24' has a upper portion 25' of a larger diameter and a threaded portion 26' of a smaller diameter that is externally threaded. A shank 27' is fixed to threaded portion 26' and to a ring or an isotropic cylinder 28'. Vane 16' is welded in a fixed position and extends through the wall thereof at locations 180 degrees apart along its opposite edges to cylinder 28'.

Pipeline 19' has a hollow cylindrical projection 29' permitting probe 11' to be threaded and lowered thereinto, projection 29' having an axis perpendicular to the axis of pipeline 19'. Projection 29' is internally threaded at 30'. Probe portion 26' is threaded into projection 29' at the thread 30'. Projection 29' has an O-ring groove 31', and an O-ring 32' therein that seals with a shoulder, not visible in FIG. 2, at the bottom of body 24' where the diameter of the probe is reduced to the diameter of the threaded portion 26' thereof. The bottom surface of the body 24' may be flat and in a plane perpendicular to the vertical axis of the probe 11' so as to rest on O-ring 32', O-ring 32' thereby sealing probe 11' inside pipeline 19'. At least that portion of probe 11' below the thread 26', thus, protrudes downwardly inside pipeline 19' below the inside diameter thereof. When probe 11' is located in pipeline 19', it is turned 90 degrees from the position shown in FIG. 2.

Figure 3:
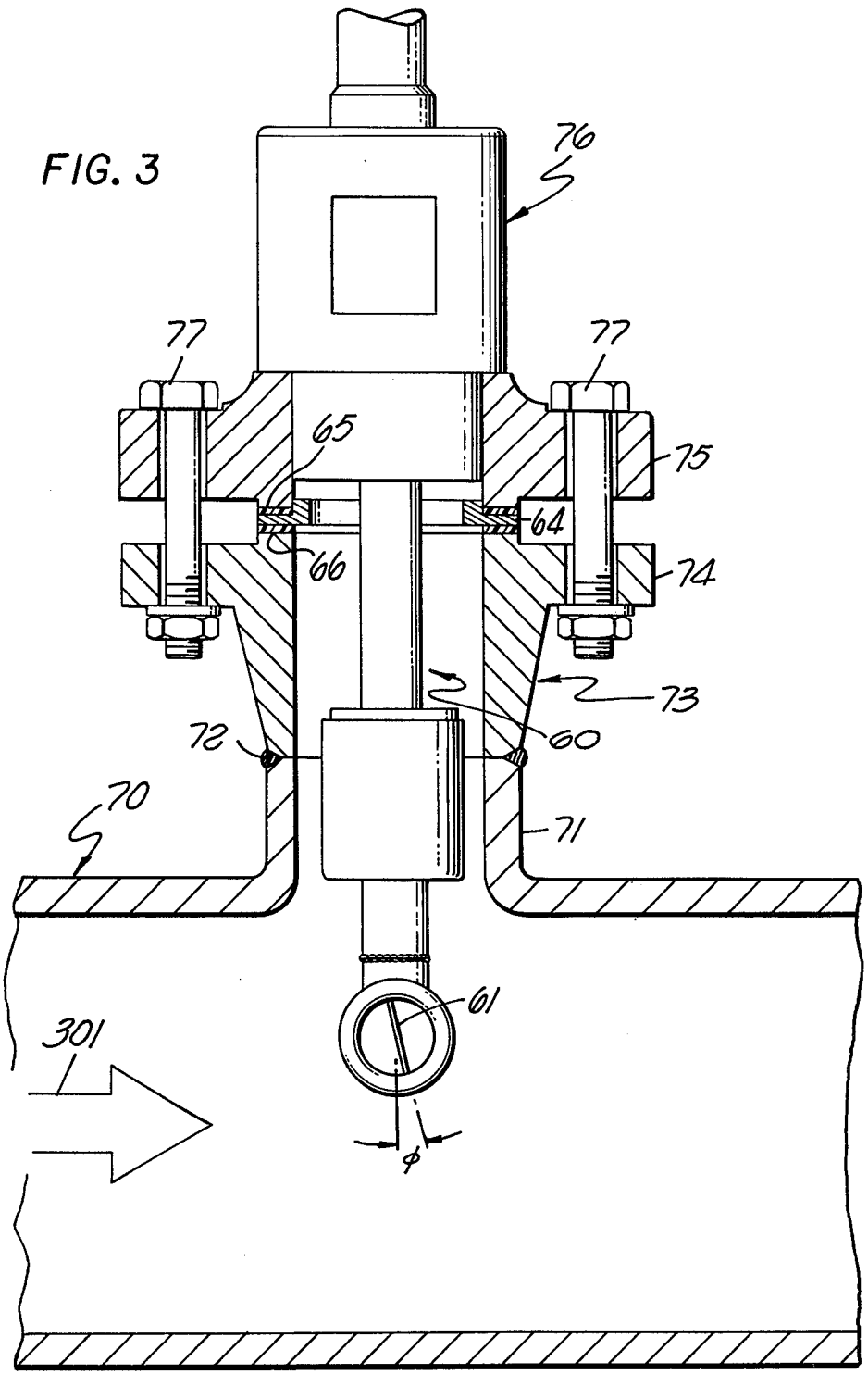
FIG. 3 is a vertical sectional view, partly in elevation, of a pipeline having a vibration densitometer probe constructed and mounted in accordance with a second embodiment of the present invention.

One embodiment of the present invention is illustrated in FIG. 2. Another embodiment is illustrated in FIG. 3. A densitometer probe 60 is shown in FIG. 3 including a vane 61. A ring 64 has annular gaskets 65 and 66 bonded onto opposite sides thereof.

Fluid flow is in the direction of an arrow 301.

A pipeline is illustrated at 70 having a hollow cylindrical projection 71 which is welded at 72 to a fitting 73. Fitting 73 has a flange 74 bolted to a flange 75 of an assembly 76 at preferably three or more or, for example, eight places 77.

The angle φ is a small acute angle of, for example, a few degrees or less. Its extent in FIG. 3 is exaggerated for clarity.

Figure 4:
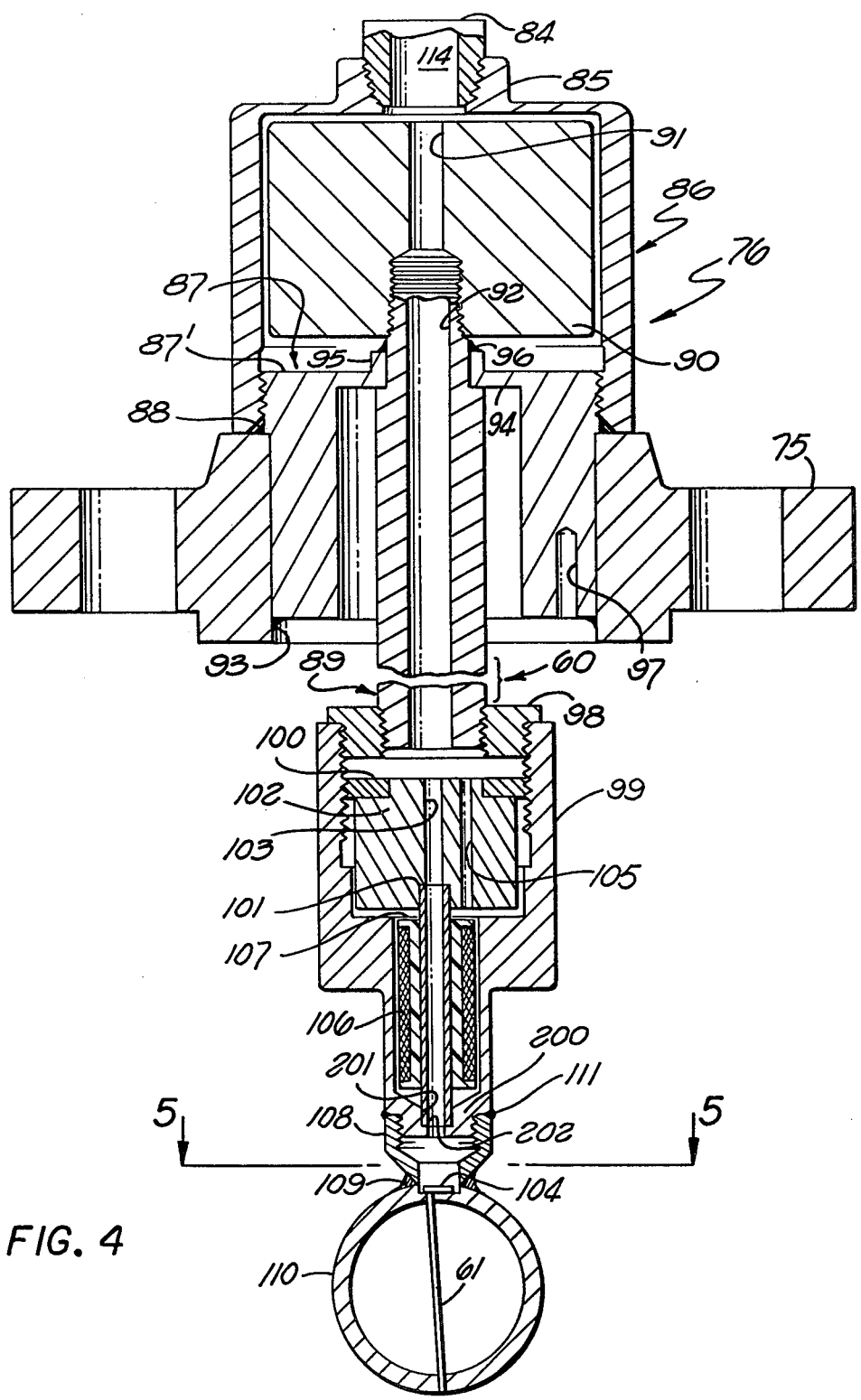
FIG. 4 is a vertical sectional view of a portion of the probe of FIG. 3.

A vertical sectional view of probe 60 is shown in FIG. 4 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 and may be welded thereto, if desired. Cylinder 90 is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pinhole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto and also welded thereto, if desired.

A ring 100 is threaded into body 99. A magnetostrictive tube 101 which is hollow and open at both ends is press fit into a body 102 and press fit into the lower end 200 of body 99. Body 102 is similar to a body disclosed in the U.S. Pat. No. 3,741,000, issued June 26, 1973, and may be identical thereto, if desired. Alternatively, body 102 may have one hole 103 to receive lead wires from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends at the bottom thereof, through a circular hole 201 in the end 200 of body 99. Bore 201 has a shoulder 202 that the lower end of tube 101 abuts.

Figures 5, 6:
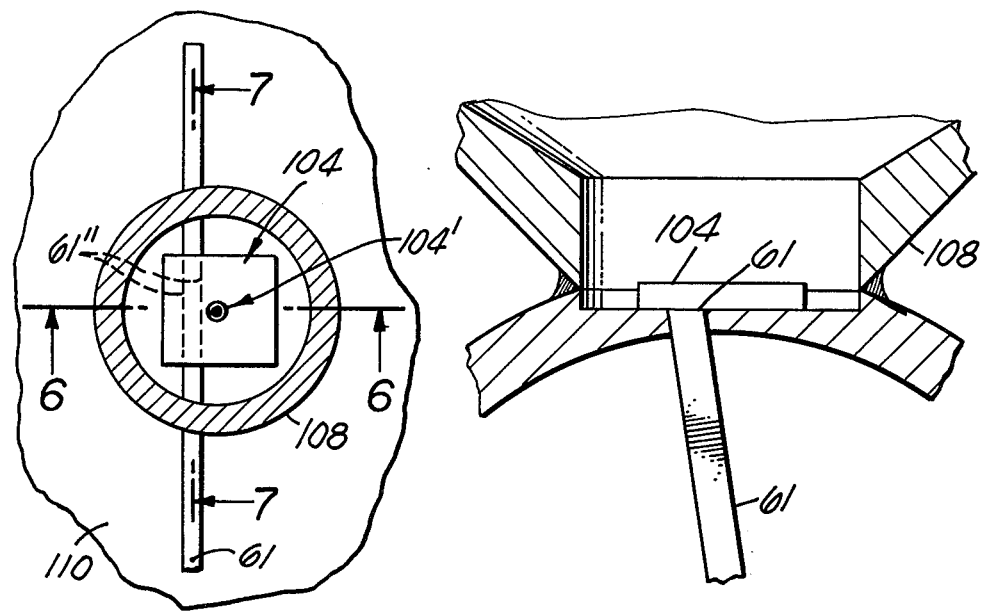
FIG. 5 is an enlarged transverse sectional view taken on the line 5—5 of the embodiment shown in FIG. 4.
FIG. 6 is an enlarged vertical sectional view of the embodiment taken on the line 6—6 shown in FIG. 5.

Crystal 104 may be square and preferrably has a central axis 104' in FIG. 5 normal to the plane of the drawing and the same as that concentric with tube 101.

Vane 61 is welded through slots in cylinder 110 that are set back from the ends thereof in a manner identical to that shown at A in FIG. 2.

Cylinder 110, vane 61, and crystal 104, fixed to cylinder 110, may be similar to those disclosed in the last mentioned patent, if desired.

A more detailed explanation of the operation of a vibration densitometer employing the structure disclosed herein is set forth in the said patents. The operation is generally the same for the present invention, except as noted herein.

It is common to use a preamplifier in the probe. Such a preamplifier may be employed at 114 in FIG. 4, or at any other convenient location, as desired.

When probe 60 is used in the system of either one of the said patents, the system may be constructed so that utilization means 14" (FIG. 1) can be an indicator which will read in pounds per cubic foot, for example.

Above weld 111 in FIG. 4, the probe 60 may be completely conventional, if desired. Body 99 and everything in FIG. 1 may also be conventional except probe 11'.

Some of the structures of the present invention new in the art reside in the mounting of crystal 104 inside ferrule 108 (the shape of ferrule 108, itself, is new). Further, the use of an angle φ (FIG. 3) for vanes 16' or 61 substantially smaller than 90 degrees, but larger than zero ($90 > > \phi > 0$) is new in the art. It is also new in the art to employ a cylinder 110 made of an isotropic material. In the prior art two cylinders or the like were employed that had an interference fit.

Crystal 104 is square as shown in FIG. 5.

From FIG. 6 it will be noted that the end surface 61' of vane 61 is spaced from, off center, and off the axis 104' (FIG. 5) of crystal 104 through it is parallel to one side of crystal 104. See dotted lines 61" in FIG. 5.

Cylinder 110 is slotted. Vane 61 then slidably mounted in these slots and is soldered or welded to cylinder 110 in the position shown in FIG. 8. Before weld 109 (FIG. 4) is made.

Figure 7:
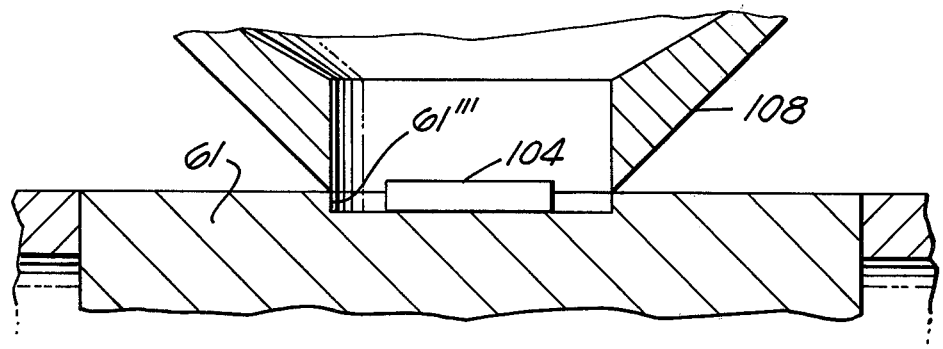
FIG. 7 is a vertical sectional view, taken on the line 7—7, shown in FIG. 5.
Figure 8:
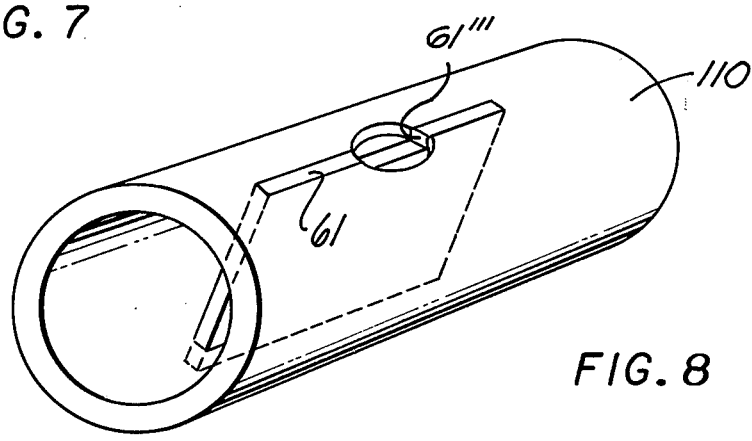
FIG. 8 is a perspective view of a subassembly of a cylinder and vane fixed together in one step performed during fabrication of the embodiment of the present invention shown in FIGS. 3-7.

As shown in FIGS. 7 and 8, vane 61 has a notch at 61'''.

According to one aspect of the present invention, angle φ is between about 0.6 and 12.0 degrees. According to another aspect of the present invention, the angle φ is about 1.2 degrees.

Cylinder 110 may be made of an isotropic material. Cylinder 110 may have an inside diameter large in comparison to the thickness of said vane 61. Cylinder 110 may have a total surface area substantially larger than that area over which it is contacted by all structures in contact therewith.

What is claimed is:

1. In a vibration densitometer, the combination comprising: a probe having a body; a magnetostrictive member mounted in said body in a position with its ends fixed to said body; means mounted in said body to vary magnetic flux through said member in a manner to cause it to expand and to contract alternately along a drive axis, said expansion and contraction causing said body to vibrate; a hollow cylinder having an external cylindrical surface with a symmetrical axis; connection means mounting said cylinder on said body in a position such that said symmetrical axis is normal to said drive axis, vibration of said body causing vibration of said hollow cylinder, said connection means having a hollow interior providing free and open communication from an exposed portion of the said external cylindrical surface of said cylinder through said body; a piezoelectric crystal bonded to said exposed portion; and a rectangular vane having two parallel edge portions fixed to said cylinder at positions 180 degrees therearound with respect to each other, said cylinder having at least one slot therethrough through which one of said two edge portions projects to a position in engagement with said crystal, said vane lying approximately in a plane through said symmetrical axis at a predetermined angle φ relative to said drive axis, said connection means being sealed to said body and sealed to said cylinder around said exposed portion thereof to prevent fluid from entering said body through the said hollow interior of said connection means.

2. The invention as defined in claim 1 wherein said cylinder is made of an isotropic material, said cylinder having an inside diameter large in comparison to the thickness of said vane, said cylinder having a total surface area substantially larger than that area over which it is contacted by all structures in contact therewith.

3. The invention as defined in claim 1 wherein said predetermined angle φ is defined in degrees thus: $90 > > \phi > 0$.

4. The invention as defined in claim 3 wherein said cylinder is made of an isotropic material, said cylinder having a inside diameter large in comparison to the thickness of said vane, said cylinder having a total surface area substantially larger than that area over which it is contacted by all structures in contact therewith.

5. The invention as defined in claim 3 wherein $\phi$ is between about 0.6 and 12.0 degrees.

6. The invention as defined in claim 5 wherein said cylinder is made of an isotropic material, said cylinder having an inside diameter large in comparison to the thickness of said vane, said cylinder having a total surface area substantially larger than that area over which it is contacted by all structures in contact therewith.

7. The invention as defined in claim 3 wherein $\phi$ is about 1.2 degrees.

8. The invention as defined in claim 7 wherein said cylinder is made of an isotropic material, said cylinder having an inside diameter large in comparison to the thickness of said vane, said cylinder having a total surface area substantially larger than that area over which it is contacted by all structures in contact therewith.

* * * * *